(12) United States Patent
Abe et al.

(10) Patent No.: US 11,701,359 B2
(45) Date of Patent: Jul. 18, 2023

(54) EXON 18 AND/OR EXON 21 MUTANT EGFR SELECTIVE INHIBITOR

(71) Applicant: Taiho Pharmaceutical Co., Ltd., Tokyo (JP)

(72) Inventors: Naomi Abe, Tsukuba (JP); Shinichi Hasako, Tsukuba (JP)

(73) Assignee: Taiho Pharmaceutical Co., Ltd., Tokyo (JP)

( * ) Notice: Subject to any disclaimer, the term of this patent is extended or adjusted under 35 U.S.C. 154(b) by 86 days.

(21) Appl. No.: 16/642,969

(22) PCT Filed: Aug. 31, 2018

(86) PCT No.: PCT/JP2018/032314
§ 371 (c)(1),
(2) Date: Feb. 28, 2020

(87) PCT Pub. No.: WO2019/045036
PCT Pub. Date: Mar. 7, 2019

(65) Prior Publication Data
US 2020/0253975 A1  Aug. 13, 2020

(30) Foreign Application Priority Data
Sep. 1, 2017  (JP) ................................. 2017-168606

(51) Int. Cl.
*A61K 31/519*  (2006.01)
*A61P 35/00*  (2006.01)

(52) U.S. Cl.
CPC ............ *A61K 31/519* (2013.01); *A61P 35/00* (2018.01)

(58) Field of Classification Search
CPC .............................. A61K 31/519; A61P 35/00
See application file for complete search history.

(56) References Cited

U.S. PATENT DOCUMENTS

| | | | |
|---|---|---|---|
| 5,733,918 A | 3/1998 | Okazaki et al. | |
| 8,119,142 B2 | 2/2012 | Zwijsen et al. | |
| 8,889,666 B2 | 11/2014 | Sagara et al. | |
| 8,912,181 B2 | 12/2014 | Kitade et al. | |
| 2014/0057899 A1 | 2/2014 | Sagara et al. | |
| 2014/0343038 A1 | 11/2014 | Sakamoto et al. | |
| 2014/0378409 A1 | 12/2014 | Fujita et al. | |
| 2016/0194332 A1 | 7/2016 | Uno et al. | |
| 2017/0101414 A1 | 4/2017 | Uno et al. | |
| 2020/0253975 A1 | 8/2020 | Abe et al. | |

FOREIGN PATENT DOCUMENTS

| | | |
|---|---|---|
| CN | 1130903 A | 9/1996 |
| CN | 102471335 A | 5/2012 |
| CN | 105683195 A | 6/2016 |
| EP | 2722332 A1 | 4/2014 |
| EP | 2960241 A1 | 12/2015 |
| EP | 3037424 A1 | 6/2016 |
| JP | 2008-533172 A | 8/2008 |
| JP | 2016-213072 A | 12/2016 |
| KR | 10-2016-0043114 A | 4/2016 |
| WO | 2006/102079 A1 | 9/2006 |
| WO | 2011/046964 A2 | 4/2011 |
| WO | 2012/093708 A1 | 7/2012 |
| WO | 2013/047813 A1 | 4/2013 |
| WO | 2013/100014 A1 | 7/2013 |
| WO | 2013/118817 A1 | 8/2013 |
| WO | 2013/125709 A1 | 8/2013 |
| WO | 2014/129596 A1 | 8/2014 |
| WO | 2015/025936 A1 | 2/2015 |
| WO | 2015/175632 A1 | 11/2015 |
| WO | 2015/195228 A1 | 12/2015 |

OTHER PUBLICATIONS

Bronto. Frontiers in Bioscience E3, 2011, 879-887 (Year: 2011).*
Kumar. Journal of Clinical Oncology, 2008, 10(1), 1742-1751 (Year: 2008).*
Hasako. Molecular Cancer Therapeutics, 2010, 17(8), 1648-1658 (Year: 2010).*
Oxnard et al. "Natural history and molecular charactertistics of lung cancers harboring EGFR exon 20 insertions," J Thorac Oncol, 2013, 8(2):179-184.
Sasaki et al. "EGFR exon 20 insertion mutation in Japanese lung cancer," Lung Cancer, 2007, 58:324-328.
Yasuda et al. "EGFR exon 20 insertion mutations in non-small-cell lung cancer: preclinical data and clinical implications" The medical frontline, 2011, Lancet Oncol 2012; 13: e23-31.
Hirano et al. "In vitro modeling to determine mutation specificity of EGFR tyrosine kinase inhibitors against clinically relevant EGFR mutants in non-small-cell lung cancer", Oncotarget, 2015, 6(36):38789-38803.
Jia et al. "EGF816 Exerts Anticancer Effects in Non-Small Cell Lung Cancer by Irreversibly and Selectively Targeting Primary and Acquired Activating Mutations in the EGF Receptor", Cancer Research, 2016, 76(6): 1591-1602.
Yasuda et al. "Structual, Biochemical, and Clinical Characterization of Epidermal Growth Factor Receptor (EGFR) Exon 20 Insertion Mutations in Lung Cancer", Science Translational Medicine, 2013, 5(214-216):135-144.
International Search Report for PCT/JP2017/037186 dated Dec. 19, 2017.
Lacouture, Mario E. "Mechanisms of cutaneous toxicities to EGFR inhibitors", Nat. Rev. Cancer, vol. 6, pp. 803-812 (2006).
Chong et al. "The quest to overcome resistance to EGFR-targeted therapies in cancer" Nature Medicine, vol. 19, pp. 1389-1400 (2013).

(Continued)

*Primary Examiner* — Noble E Jarrell
(74) *Attorney, Agent, or Firm* — Oblon, McClelland, Maier & Neustadt, L.L.P.

(57) ABSTRACT

An antitumor agent for treating a malignant tumor patient expressing EGFR having at least one mutation selected from the group consisting of G719X mutation of exon 18, E709X mutation of exon 18, and L861X mutation of exon 21, wherein X represents an arbitrary amino-acid residue, the antitumor agent comprising (S)-N-(4-amino-6-methyl-5-(quinolin-3-yl)-8,9-dihydropyrimido[5,4-b]indolizin-8-yl) acrylamide or a salt thereof.

28 Claims, 4 Drawing Sheets
Specification includes a Sequence Listing.

(56) References Cited

OTHER PUBLICATIONS

Sharma et al."Epidermal growth factor receptor mutations in lung cancer" Nat. Rev. Cancer, vol. 7, pp. 169-181 (2007).
Li et al. "Design and implementation of the MMC simulation system in the heterogeneous FPGA-CPU platform" Lancet Oncol. vol. 13, e. 23-31 (2012).
Yang et al. Clinical activity of afatinib in patients with advanced non-small-cell lung cancer harbouring uncommon EGFR mutations: a combined post-hoc analysis of LUX-Lung 2, LUX-Lung 3, and LUX-Lung 6; Lancet Oncol. vol. 16, pp. 830-838 (2015).
Yasuda, Hiroyuki "EGFR Exon 20 Insertion Mutations in Lung Cancer" Aug. 2016, vol. 71, No. 8, pp. 1721-1725.
Naidoo et al.: Epidermal growth factor receptor exon 20 insertions in advanced lung adenocarcinomas: Clinical outcomes and response to erlotinib : EGFR Exon 20 Insertions11, Cancer., vol. 121, No. 18, Jun. 10, 2015 (Jun. 10, 2015), pp. 3212-3220.
Naidoo et al. "EGFRexon 20 insertions in advanced lung adenocarcinomas: clinical outcomes and response to erlotinib" Cancer. Sep. 15, 2015; 121(18): 3212-3220.
Arteaga "The Epidermal Growth Factor Receptor: From Mutant Oncogene in Nonhuman Cancers to Therapeutic Target in Human Neoplasia", Journal of Clinical Oncology, 2001, vol. 19, No. 18s, pp. 32s-40s.
Ministry of Internal Affairs and Communications Statistics Bureau homepage | statistical data / world statistics "World Statistics 2011", p. 332 14-1.
Doebele et al., "New strategies to overcome limitations of reversible EGFR tyrosine kinase inhibitor therapy in non-mall cell lung cancer", Lung Cancer, 2010, vol. 69, No. 1, pp. 1-12.
Pao et al., "Rational, biologically based treatment of EGFR-mutant non-small-cell lung cancer", Nature Reviews Cancer, 2010, vol. 10, No. 11, pp. 760-774.
International Preliminary Report on Patentability for PCT/JP2019/051377, dated Jul. 8, 2021, 8 pages.
Wei, Y., et al., "Three new disease-progression modes in NSCLC patients after EGFR-TKI treatment by next-generation sequencing analysis", Lung Cancer, Elsevier, vol. 125, Sep. 1, 2018, pp. 43-50.
Yang et al. "Clinical activity of afatinib in patients with advanced non-small-cell lung cancer harbouring uncommon EGFR mutations: a combined post-hoc analysis of LUX-Lung 2, LUX-Lung 3, and LUX-Lung 6," Lancet Oncol., 2015, 16(7):830-8.
Kobayashi et al. "Not all epidermal growth factor receptor mutations in lung cancer are created equal: Perspectives tor individualized treatment strategy," Cancer Sci., 2016, 107(9):1179-86.
Nishino et al. "Guidelines of examination about EGFR gene mutations in lung cancer patient," ver. 3. 05, [online], 2016, [retrieval date Feb. 25, 2020], internet<URL:https://haigan.gr.jp/uploads/files/photos/1329.pdf>, machine translation.
International Search Report for PCT/JP2018/032314 dated Oct. 30, 2018.
Wee et al., "Epidermal Growth Factor Receptor Cell Proliferation Signaling Pathways", Cancers (Basel), 2017, 71 pages, [retrieved on Jul. 5, 2022], Retrieved from the Internet <URL: https://www.ncbi.nlm.nih.gov/pmc/articles/PMC5447962/>.
Extended European Search Report dated Apr. 14, 2021, in corresponding European Patent Application No. 18851555.5, 7 pages.
Combined Taiwanese Office Action and Search Report dated Jun. 6, 2022, in corresponding Taiwanese Patent Application No. 107130585 (with English Translation of Category of Cited Documents), 6 pages.
Hasako et al., "TAS6417, A Novel EGFR Inhibitor Targeting Exon 20 Insertion Mutations", Molecular Cancer Therapeutics, 2018, vol. 17, No. 8, pp. 1648-1658.
Hasako et al., "Abstract A158: Characterization of antitumor activity of TAS6417, a novel EGFR-TKI targeting exon 20 insertions", Molecular Cancer Therapeutics, vol. 17, No. 1, Supplement 1, 2018, p. A158.
Shan et al., "EGFR Mutation Status in Uighur Lung Adenocarcinoma Patients", Chin J Lung Cancer, 2013, vol. 16, No. 2, pp. 78-81 (with English Abstract).
Hasako et al., "TPC-064, a novel mutant-selective EGFR inhibitor, targets NSCLC driven by EGFR exon 20 insertion mutations", Poster for 28th EORTC—NCI—AACR Symposium on Molecular Targets and Cancer Therapeutics, 2016.
Hasako et al., "Characterization of antitumor activity of TAS6417, a novel EGFR-TKI targeting exon 20 insertions", Poster for AACR-NCI-EORTC International Conference on Molecular Targets and Cancer Therapeutics, 2018.
Hasako et al., "In vitro and in vivo activity of TAS6417 against uncommon EGFR mutations", Poster for AACR-NCI-EORTC, 2018.
Udagawa et al., "Preclinical evaluation of TAS6417 as a highly effective, pan-mutation-selective EGFR tyrosine kinase inhibitor", Poster for AACR2019, 2019.
Kobayashi, "Resistance to EGFR Tyrosine Kinase Inhibitors", Presentation document at The 34th Nagoya International Cancer Treatment Symposium, 2019.
Udagawa et al., "TAS6417/CLN-081 Is a Pan-Mutation-Selective EGFR Tyrosine Kinase Inhibitor with a Broad Spectrum of Preclinical Activity against Clinically Relevant EGFR Mutations", Molecular Cancer Research, 17(11), 2019, pp. 2233-2243.
Kobayashi, "Development of novel strategies to overcome resistance to targeted therapies", Presentation document at JSMO annual meeting, 2019, 27 pages.
Piotrowska et al., "Multicenter Phase 1/2a trial of CLN-081 (TAS6417) in NSCLC Patients with EGFR Exon 20 Insertion Mutations", Poster for World Conference on Lung Cancer, 2019.
Kobayashi et al., "Compound EGFR Mutationsand Response to EGFR Tyrosine Kinase Inhibitors", Journal of Thoracic Oncology, 2013, vol. 8, No. 1, pp. 118-122.
Office Action dated Sep. 20, 2022 for the corresponding CN patent application No. 201880064210.3, 24 pages (with English Translation).

\* cited by examiner

SEQUENCE LISTING

<160> NUMBER OF SEQ ID NOS: 1

<210> SEQ ID NO 1
<211> LENGTH: 1210
<212> TYPE: PRT
<213> ORGANISM: Homo sapiens

<400> SEQUENCE: 1

```
Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
                20                  25                  30

Gly Thr Ser Asn Lys Leu Thr Gln Leu Gly Thr Phe Glu Asp His Phe
            35                  40                  45

Leu Ser Leu Gln Arg Met Phe Asn Asn Cys Glu Val Val Leu Gly Asn
50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
```

-continued

```
                210                 215                 220
Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
                260                 265                 270

Thr Thr Tyr Gln Met Asp Val Asn Pro Glu Gly Lys Tyr Ser Phe Gly
            275                 280                 285

Ala Thr Cys Val Lys Lys Cys Pro Arg Asn Tyr Val Val Thr Asp His
        290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
                340                 345                 350

Ala Thr Asn Ile Lys His Phe Lys Asn Cys Thr Ser Ile Ser Gly Asp
            355                 360                 365

Leu His Ile Leu Pro Val Ala Phe Arg Gly Asp Ser Phe Thr His Thr
            370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
                420                 425                 430

His Gly Gln Phe Ser Leu Ala Val Val Ser Leu Asn Ile Thr Ser Leu
            435                 440                 445

Gly Leu Arg Ser Leu Lys Glu Ile Ser Asp Gly Asp Val Ile Ile Ser
450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
                500                 505                 510

Glu Gly Cys Trp Gly Pro Glu Pro Arg Asp Cys Val Ser Cys Arg Asn
            515                 520                 525

Val Ser Arg Gly Arg Glu Cys Val Asp Lys Cys Asn Leu Leu Glu Gly
        530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
                580                 585                 590

Lys Thr Cys Pro Ala Gly Val Met Gly Glu Asn Asn Thr Leu Val Trp
            595                 600                 605

Lys Tyr Ala Asp Ala Gly His Val Cys His Leu Cys His Pro Asn Cys
        610                 615                 620

Thr Tyr Gly Cys Thr Gly Pro Gly Leu Glu Gly Cys Pro Thr Asn Gly
625                 630                 635                 640
```

```
Pro Lys Ile Pro Ser Ile Ala Thr Gly Met Val Gly Ala Leu Leu Leu
            645                 650                 655
Leu Leu Val Val Ala Leu Gly Ile Gly Leu Phe Met Arg Arg Arg His
            660                 665                 670
Ile Val Arg Lys Arg Thr Leu Arg Arg Leu Leu Gln Glu Arg Glu Leu
            675                 680                 685
Val Glu Pro Leu Thr Pro Ser Gly Glu Ala Pro Asn Gln Ala Leu Leu
            690                 695                 700
Arg Ile Leu Lys Glu Thr Glu Phe Lys Lys Ile Lys Val Leu Gly Ser
705                 710                 715                 720
Gly Ala Phe Gly Thr Val Tyr Lys Gly Leu Trp Ile Pro Glu Gly Glu
                725                 730                 735
Lys Val Lys Ile Pro Val Ala Ile Lys Glu Leu Arg Glu Ala Thr Ser
                740                 745                 750
Pro Lys Ala Asn Lys Glu Ile Leu Asp Glu Ala Tyr Val Met Ala Ser
                755                 760                 765
Val Asp Asn Pro His Val Cys Arg Leu Leu Gly Ile Cys Leu Thr Ser
770                 775                 780
Thr Val Gln Leu Ile Thr Gln Leu Met Pro Phe Gly Cys Leu Leu Asp
785                 790                 795                 800
Tyr Val Arg Glu His Lys Asp Asn Ile Gly Ser Gln Tyr Leu Leu Asn
                805                 810                 815
Trp Cys Val Gln Ile Ala Lys Gly Met Asn Tyr Leu Glu Asp Arg Arg
                820                 825                 830
Leu Val His Arg Asp Leu Ala Ala Arg Asn Val Leu Val Lys Thr Pro
                835                 840                 845
Gln His Val Lys Ile Thr Asp Phe Gly Leu Ala Lys Leu Leu Gly Ala
                850                 855                 860
Glu Lys Glu Tyr His Ala Glu Gly Gly Lys Val Pro Ile Lys Trp
865                 870                 875                 880
Met Ala Leu Glu Ser Ile Leu His Arg Ile Tyr Thr His Gln Ser Asp
                885                 890                 895
Val Trp Ser Tyr Gly Val Thr Val Trp Glu Leu Met Thr Phe Gly Ser
                900                 905                 910
Lys Pro Tyr Asp Gly Ile Pro Ala Ser Glu Ile Ser Ser Ile Leu Glu
                915                 920                 925
Lys Gly Glu Arg Leu Pro Gln Pro Pro Ile Cys Thr Ile Asp Val Tyr
930                 935                 940
Met Ile Met Val Lys Cys Trp Met Ile Asp Ala Asp Ser Arg Pro Lys
945                 950                 955                 960
Phe Arg Glu Leu Ile Ile Glu Phe Ser Lys Met Ala Arg Asp Pro Gln
                965                 970                 975
Arg Tyr Leu Val Ile Gln Gly Asp Glu Arg Met His Leu Pro Ser Pro
                980                 985                 990
Thr Asp Ser Asn Phe Tyr Arg Ala Leu Met Asp Glu Glu Asp Met Asp
                995                 1000                1005
Asp Val Val Asp Ala Asp Glu Tyr Leu Ile Pro Gln Gln Gly Phe
                1010                1015                1020
Phe Ser Ser Pro Ser Thr Ser Arg Thr Pro Leu Leu Ser Ser Leu
                1025                1030                1035
Ser Ala Thr Ser Asn Asn Ser Thr Val Ala Cys Ile Asp Arg Asn
                1040                1045                1050
```

-continued

```
Gly Leu Gln Ser Cys Pro Ile Lys Glu Asp Ser Phe Leu Gln Arg
    1055            1060            1065

Tyr Ser Ser Asp Pro Thr Gly Ala Leu Thr Glu Asp Ser Ile Asp
    1070            1075            1080

Asp Thr Phe Leu Pro Val Pro Glu Tyr Ile Asn Gln Ser Val Pro
    1085            1090            1095

Lys Arg Pro Ala Gly Ser Val Gln Asn Pro Val Tyr His Asn Gln
    1100            1105            1110

Pro Leu Asn Pro Ala Pro Ser Arg Asp Pro His Tyr Gln Asp Pro
    1115            1120            1125

His Ser Thr Ala Val Gly Asn Pro Glu Tyr Leu Asn Thr Val Gln
    1130            1135            1140

Pro Thr Cys Val Asn Ser Thr Phe Asp Ser Pro Ala His Trp Ala
    1145            1150            1155

Gln Lys Gly Ser His Gln Ile Ser Leu Asp Asn Pro Asp Tyr Gln
    1160            1165            1170

Gln Asp Phe Phe Pro Lys Glu Ala Lys Pro Asn Gly Ile Phe Lys
    1175            1180            1185

Gly Ser Thr Ala Glu Asn Ala Glu Tyr Leu Arg Val Ala Pro Gln
    1190            1195            1200

Ser Ser Glu Phe Ile Gly Ala
    1205            1210
```

EXON 18 AND/OR EXON 21 MUTANT EGFR SELECTIVE INHIBITOR

CROSS REFERENCE TO RELATED APPLICATION

This application is a United States National Phase Application under 35 U.S.C. § 371 of International Application PCT/JP2018/032314 filed on Aug. 31, 2018, which claims priority from Application 2017-168606 filed on Sep. 1, 2017 in Japan. The entire contents of each these applications are incorporated herein by reference in their entirety.

TECHNICAL FIELD

The present invention relates to an antitumor agent against cancers, comprising an exon 18 and/or exon 21 mutant epidermal growth factor receptor (hereinafter also referred to as "EGFR").

BACKGROUND ART

EGFR is a receptor-type tyrosine kinase, exerts its physiological function in normal tissue by being bound to Epidermal Growth Factor (hereinafter also referred to as EGF), which is a ligand, and contributes to growth and apoptosis inhibition in epithelial tissues (NPL 1). Further, somatic mutation of EGFR gene has been known as a cancer-causing gene; for example, EGFR in which codons 746 to 750 in exon 19 are deleted (hereinafter also referred to as "exon 19 deletion mutation") and EGFR in which leucine encoded by codon 858 in exon 21 is mutated to arginine (hereinafter also referred to as "L858R mutation") constantly induces EGF-independent kinase activity, and contributes to the growth and survival of cancer cells (NPL 2). These mutations are observed, for example, in 30 to 50% of non-small-cell lung cancer in East Asia. The mutations are also observed in about 10% of non-small-cell lung cancer in Europe and the United States, and are regarded as one of the causes of cancers (NPL 3).

Therefore, research and development of EGFR inhibitor as an antitumor agent have actively been conducted, and introduced into the treatment of various EGFR mutation-positive lung cancers (NPL 2 and NPL 4). Gefitinib, erlotinib, and afatinib have been used as a therapeutic agent against exon 19 deletion mutant and L858R mutant EGFR-positive lung cancers. Exon 19 deletion mutation and L858R mutation account for 90% of EGFR mutation. Further, occurrence of acquired resistance in the process of the treatment using these agents has been known, and 50% thereof is caused by resistance mutation EGFR in which codon 790 of exon 20 is changed from threonine to methionine (hereinafter also referred to as "T790M mutation"). To treat lung cancers having this mutation, osimertinib has been used as a therapeutic agent. Therefore, treatments using EGFR inhibitors are in the process of being established for lung cancer patients having major EGFR mutations.

On the other hand, at present, no treatments using EGFR inhibitors have been established with respect to some rare EGFR mutations, such as point mutation or deletion mutation of exon 18, point mutation of exon 21, or the like; and there are reports that the drug sensitivity of these mutant EGFR varies depending on the mutation type (NPL 4). For example, the sensitivity of the lung cancer having point mutation in which glycine encoded by codon 719 of exon 18 is substituted with an arbitrary amino acid (hereinafter also referred to as "G719X mutation") or the lung cancer in which leucine encoded by codon 861 of exon 21 is substituted with glutamine (hereinafter also referred to as "L861Q mutation") with respect to gefitinib, erlotinib, and afatinib is lower than those of exon 19 deletion mutation and L858R mutation, which are drug-sensitive mutations. Further, there are reports of skin disorders and digestive tract disorders as common side effects by the administration of therapeutic doses of afatinib, gefitinib, and erlotinib. It is widely thought that these side effects are attributable to inhibition of the function of wild-type EGFR expressed in normal tissues, such as skin or digestive tract, by the therapeutic agent (NPL 1); the development of an inhibitor characterized by lower inhibitory activity with respect to wild-type EGFR of normal tissues, compared with mutant EGFR expressed in tumor tissues, has been desired in view of reduction of side effects.

Therefore, development of a drug having high inhibitory activity with respect to exon 18 and exon 21 mutant EGFR, as well as high selectivity with respect to mutant EGFR compared with wild-type EGFR, is expected to enable inhibition of growth of lung cancer cells having mutant EGFR with a dose lower than the dose causing the side effects in the skin or digestive tract, thereby contributing to life prolongation or increase in QOL of patients with mutant EG1-R-positive cancers for which treatment methods have not been established. Further, a drug having high inhibitory activity with respect to T790M, which is acquired resistance mutation against treatments using EGFR inhibitors, is expected to reduce expression frequency of acquired resistance during the treatments using EGFR inhibitors against exon 18 or exon 21 mutant EGFR, which is de novo mutation; and is therefore expected to contribute to the life prolongation of cancer patients.

CITATION LIST

Patent Literature

PTL 1: WO2015/175632A1
PTL 2: WO2015/025936A1

Non-Patent Literature

NPL 1: Nat. Rev. Cancer, Vol. 6, pp. 803-812 (2006)
NPL 2: Nature Medicine, Vol. 19, pp. 1389-1400 (2013)
NPL 3: Nat. Rev. Cancer, Vol. 7, pp. 169-181(2007)
NPL 4: Lancet Oncol. Vol. 13, e. 23-31 (2012)

SUMMARY OF INVENTION

Technical Problem

An object of the present invention is to provide an antitumor agent that does not cause inhibition of wild-type EGFR and thus causes smaller side effects, serving as an inhibitor that can ensure high selectivity with respect to exon 18 and/or exon 21 mutant EGFR for which the therapeutic effects of the previously known EGFR inhibitors are insufficient.

Solution to Problem

The inventors of the present invention conducted extensive research, and found that exon 18 and/or exon 21 mutant EGFR is an appropriate target in treating cancers, and that EGFR inhibitors conventionally used for the treatments have inferior selectivity between exon 18 and/or exon 21 mutant EGFR. Further, the inventors also confirmed that the compound of the present invention exerts superior selectivity and tumor growth inhibitory effects with respect to exon 18 and/or exon 21 mutant EGFR. With this finding, the inventors accomplished the present invention.

The present invention encompasses the following embodiments.

Item 1.

An antitumor agent for treating a malignant tumor patient expressing EGFR having at least one mutation selected from the group consisting of G719X mutation of exon 18, E709X mutation of exon 18, and L861X mutation of exon 21, wherein X represents an arbitrary amino-acid residue, the antitumor agent comprising (S)-N-(4-amino-6-methyl-5-(quinolin-3-yl)-8,9-dihydropyrimido[5,4-b]indolizin-8-yl)acrylamide or a salt thereof.

Item 2.

The antitumor agent according to Item 1, wherein the exon 18 mutation is at least one mutation selected from the group consisting of G719A, G719S, G719C, E709K and E709A.

Item 3.

The antitumor agent according to Item 1 or 2, wherein the exon 21 mutation is L861Q.

Item 4.

The antitumor agent according to any one of Items 1 to 3, wherein the EG further has T790M mutation.

Item 5.

A method for treating a malignant tumor patient, comprising the step of administering (S)-N-(4-amino-6-methyl-5-(quinolin-3-yl)-8,9-dihydropyrimido[5,4-b]indolizin-8-yl)acrylamide or a salt thereof to a malignant tumor patient expressing EGI-ilt having at least one mutation selected from the group consisting of G719X mutation of exon 18, E709X mutation of exon 18, and L861X mutation of exon 21, wherein X represents an arbitrary amino-acid residue.

Item 6.

The method according to Item 5, wherein the exon 18 mutation is at least one mutation selected from the group consisting of G719A, G719S, G719C, E709K and E709A.

Item 7.

The method according to Item 5 or 6, wherein the exon 21 mutation is L861Q.

Item 8.

The method according to any one of Items 5 to 7, wherein the EGFR further has T790M mutation.

Item 9.

(S)-N-(4-amino-6-methyl-5-(quinolin-3-yl)-8,9-dihydropyrimido[5,4-b]indolizin-8-yl)acrylamide or a salt thereof for treating a malignant tumor patient expressing EGFR having at least one mutation selected from the group consisting of G719X mutation of exon 18, E709X mutation of exon 18, and L861X mutation of exon 21, wherein X represents an arbitrary amino-acid residue.

Item 10.

The (S)-N-(4-amino-6-methyl-5-(quinolin-3-yl)-8,9-dihydropyrimido[5,4-b]indolizin-8-yl)acrylamide or a salt thereof according to Item 9, wherein the exon 18 mutation is at least one mutation selected from the group consisting of G719A, G719S, G719C, E709K and E709A.

Item 11.

The (S)-N-(4-amino-6-methyl-5-(quinolin-3-yl)-8,9-dihydropyrimido[5,4-b]indolizin-8-yl)acrylamide or a salt thereof according to Item 9 or 10, wherein the exon 21 mutation is L861Q.

Item 12.

The (S)-N-(4-amino-6-methyl-5-(quinolin-3-yl)-8,9-dihydropyrimido[5,4-b]indolizin-8-yl)acrylamide or a salt thereof according to any one of Items 9 to 11, wherein the EGFR further has T790M mutation.

Item 13.

Use of (S)-N-(4-amino-6-methyl-5-(quinolin-3-yl)-8,9-dihydropyrimido[5,4-b]indolizin-8-yl)acrylamide or a salt thereof for treating a malignant tumor patient expressing EGFR having at least one mutation selected from the group consisting of G719X mutation of exon 18, E709X mutation of exon 18, and L861X mutation of exon 21, wherein X represents an arbitrary amino-acid residue.

Item 14.

The use according to Item 13, wherein the exon 18 mutation is at least one mutation selected from the group consisting of G719A, G719S, G719C, E709K and E709A.

Item 15.

The use according to Item 13 or 14, wherein the exon 21 mutation is L861Q.

Item 16.

The use according to any one of Items 13 to 15, wherein the EGFR further has T790M mutation.

Item 17.

Use of (S)-N-(4-amino-6-methyl-5-(quinolin-3-yl)-8,9-dihydropyrimido[5,4-b]indolizin-8-yl)acrylamide or a salt thereof for the production of a pharmaceutical agent for treating a malignant tumor patient expressing EGI-ilt having at least one mutation selected from the group consisting of G719X mutation of exon 18, E709X mutation of exon 18, and L861X mutation of exon 21, wherein X represents an arbitrary amino-acid residue.

Item 18.

The use according to Item 17, wherein the exon 18 mutation is at least one mutation selected from the group consisting of G719A, G719S, G719C, E709K and E709A.

Item 19.

The use according to Item 17 or 18, wherein the exon 21 mutation is L861Q.

Item 20.

The use according to any one of Items 17 to 19, wherein the EGFR further has T790M mutation.

Item 21.

A pharmaceutical composition comprising (S)-N-(4-amino-6-methyl-5-(quinolin-3-yl)-8,9-dihydropyrimido[5,4-b]indolizin-8-yl)acrylamide or a salt thereof and a pharmaceutically acceptable carrier, for treating a malignant tumor patient expressing EGFR having at least one mutation selected from the group consisting of G719X mutation of exon 18, E709X mutation of exon 18, and L861X mutation of exon 21, wherein X represents an arbitrary amino-acid residue.

Item 22.

The pharmaceutical composition according to Item 21, wherein the exon 18 mutation is at least one mutation selected from the group consisting of G719A, G719S, G719C, E709K and E709A.

Item 23.

The pharmaceutical composition according to Item 21 or 22, wherein the exon 21 mutation is L861Q.

Item 24.

The pharmaceutical composition according to any one of Items 21 to 23, wherein the EGFR further has T790M mutation.

Item 25.

A method for predicting therapeutic effects of chemotherapy using an antitumor agent comprising, as an active ingredient, (S)-N-(4-amino-6-methyl-5-(quinolin-3-yl)-8,9- dihydropyrimido[5,4-b]indolizin-8-yl)acrylamide or a salt thereof in a malignant tumor patient, the method comprising steps (1) and (2) below:

(1) a step of detecting the presence or absence of mutation of EGFR gene contained in a biological sample obtained from the patient; and (2) a step of predicting that the chemotherapy is highly likely to exhibit sufficient therapeutic effects with respect to the patient when the results of the detection in step (1) found that the EGFR gene has at least one mutation selected from the group consisting of G719X mutation of exon 18, E709X mutation of exon 18, and L861X mutation of exon 21, wherein X represents an arbitrary amino-acid residue.

Item 26.

The method according to Item 25, wherein the exon 18 mutation is at least one mutation selected from the group consisting of G719A, G719S, G719C, E709K and E709A.

Item 27.

The method according to Item 25 or 26, wherein the exon 21 mutation is L861Q.

Item 28.

The method according to any one of Items 25 to 27, wherein the EGFR further has T790M mutation.

Item 29.

A method for treating a malignant tumor patient, comprising steps (1) to (3) below:

(1) a step of detecting the presence or absence of mutation of EGFR gene contained in a biological sample obtained from the patient;

(2) a step of predicting that chemotherapy using an antitumor agent comprising, as an active ingredient, (S)-N-(4-amino-6-methyl-5-(quinolin-3-yl)-8,9-dihydropyrimido[5,4-b]indolizin-8-yl)acrylamide or a salt thereof is highly likely to exhibit sufficient therapeutic effects with respect to the patient when the results of the detection in step (1) found that the EGFR gene has at least one mutation selected from the group consisting of G719X mutation of exon 18, E709X mutation of exon 18, and L861X mutation of exon 21, wherein X represents an arbitrary amino-acid residue; and (3) a step of administering (S)-N-(4-amino-6-methyl-5-(quinolin-3-yl)-8,9-dihydropyrimido[5,4-b]indolizin-8-yl)acrylamide or a salt thereof to a malignant tumor patient who was predicted highly likely to sufficiently respond to the chemotherapy using an antitumor agent comprising, as an active ingredient, (S)-N-(4-amino-6-methyl-5-(quinolin-3-yl)-8,9-dihydropyrimido[5,4-b]indolizin-8-yl)actylamide or a salt thereof, in step (2).

Item 30.

The method according to Item 29, wherein the exon 18 mutation is at least one mutation selected from the group consisting of G719A, G719S, G719C, E709K and E709A.

Item 31.

The method according to Item 29 or 30, wherein the exon 21 mutation is L861Q.

Item 32.

The method according to any one of Items 29 to 31, wherein the EGFR further has T790M mutation.

Advantageous Effects of Invention

The antitumor agent of the present invention exerts high selectivity with respect to exon 18 and/or exon 21 mutant EGFR. Therefore, the antitumor agent of the present invention is useful in view of providing an antitumor agent that exerts superior therapeutic effects for a malignant tumor patient expressing EGFR having exon 18 and/or exon 21 mutation, for which the therapeutic effects of the previously known EGFR inhibitors are insufficient.

The present invention is also useful in terms of providing a method for treating a malignant tumor patient expressing EGFR having exon 18 and/or exon 21 mutation.

The previously known EGFR inhibitors have low selectivity with respect to exon 18 and exon 21 mutant EGFR, compared with wild-type EGFR; therefore, the difference between the dosage for ensuring the antitumor effects and the dosage causing the side effects (skin disorders, digestive tract disorders, etc.) derived from wild-type EGFR inhibition was small. Accordingly, the previously known EGFR inhibitors have difficulty in exerting sufficient therapeutic effects. In contrast, since the antitumor agent of the present invention has high selectivity with respect to exon 18 and exon 21 mutant EGFR, it is possible to increase the dosage without causing side effects derived from wild-type EGFR inhibition. Therefore, the antitumor agent of the present invention exerts superior therapeutic effects for a malignant tumor patient expressing EGFR having exon 18 and/or exon 21 mutation.

In addition, the antitumor agent of the present invention exhibited high inhibitory activity with respect to exon 18 and exon 21 mutant EGFR in the presence of T790M mutation, which is acquired resistance mutation in the exon 20 region. Therefore, the antitumor agent of the present invention exerts superior therapeutic effects with respect to a malignant tumor patient whose response to the existing drug is low due to acquired resistance mutation caused by the use of existing antitumor agent.

Further, the antitumor agent of the present invention is also useful in terms of reducing expression frequency of acquired resistance during the treatments using EGFR inhibitors against exon 18 or exon 21 mutant EGFR, which is de novo mutation, because of its high inhibitory activity against exon 18 and exon 21 mutant EGFR even under the presence of T790M mutation, which is acquired resistance mutation in the exon 20 region.

DESCRIPTION OF EMBODIMENTS

Preferable examples of various definitions in the scope of the present invention used in this specification are explained below in detail.

In this specification, "EGFR" refers to a human epidermal growth factor receptor protein, and is also referred to as ErbB-1 or HER1.

In this specification, "wild-type EGFR" refers to EGFR free of somatic mutation, which is a protein comprising the amino acid sequence represented by SEQ ID NO: 1 (GenBank accession number: NP_005219.2).

In this specification, "exon 18" refers to 688-728 region in the amino acid sequence of wild-type EGFR (SEQ ID NO: 1).

In this specification, "exon 18 mutation" refers to point mutation in amino acid in the exon 18 region of wild-type EGFR (SEQ ID NO: 1). Preferable exon 18 mutation is point mutation or deletion mutation with 1 amino acid substitution in the exon 18 region. More preferably, the exon 18 mutation is E709X, which is point mutation in which glutamic acid encoded by codon 709 of exon 18 is substituted with an arbitrary amino acid; or G719X, which is point mutation in which glycine encoded by codon 719 of exon 18 is substituted with an arbitrary amino acid. More specifically, preferable examples of E709X include E709K, which is point mutation in which glutamic acid encoded by codon 709 in the exon 18 region is substituted with lysine; and E709A, which is point mutation in which glutamic acid encoded by codon 709 in the exon 18 region is substituted with alanine. Preferable examples of G719X include G719A, which is point mutation in which glycine encoded by codon 719 in the exon 18 region is substituted with alanine; G719S, which is point mutation in which glycine encoded by codon 719 in the exon 18 region is substituted with serine; and G719C, which is point mutation in which glycine encoded by codon 719 in the exon 18 region is substituted with cysteine. Among these, G719A is particularly preferable.

In the present invention, "exon 21" refers to 824-875 region in the amino acid sequence of wild-type EGFR (SEQ ID NO: 1).

In this specification, "exon 21 mutation" refers to point mutation in amino acid in the exon 21 region of wild-type EGFR (SEQ ID NO: 1). Preferable exon 21 mutation is point mutation with 1 amino acid substitution in the exon 21 region. More preferably, the exon 21 mutation is L861X, which is point mutation in which leucine encoded by codon 861 in the exon 21 region is substituted with an arbitrary amino acid. More specifically, L861Q, which is point mutation in which leucine encoded by codon 861 in the exon 21 region is substituted with glutamine, is preferable.

In the present invention, "exon 18 and/or exon 21 mutation" encompasses "exon 18 mutation," "exon 21 mutation," and "exon 18 and exon 21 mutation."

In the present invention, "point mutation" refers to mutation causing substitution, insertion, or deletion of one or more (e.g., about 1 to 10, preferably about 1 to 5, more preferably about 1, 2, or 3) amino-acid residues; and may include in-frame insertion and/or deletion mutation as nucleic acid.

"EGFR having exon 18 and/or exon 21 mutation" encompasses "EGFR having exon 18 mutation, " "EGFR having exon 21 mutation," and "EGFR having exon 18 and exon 21 mutation".

In this specification, the "EGFR having exon 18 mutation" refers to EGFR having at least one exon 18 mutation. The EGFR may have two or more different exon 18 mutations, and preferably has a single exon 18 mutation. Further, the EGFR may also have a mutation other than exon 18 mutation (such as exon 19 deletion mutation, L858R mutation, or L790M mutation).

In this specification, the "EGFR having exon 21 mutation" refers to EGFR having at least one exon 21 mutation. The EGFR may have two or more different exon 21 mutations, and preferably has a single exon 21 mutation. Further, the EGFR may also have a mutation other than exon 21 mutation (such as exon 19 deletion mutation, L858R mutation, or L790M mutation).

Further, EGFR having exon 18 and/or exon 21 mutation may further have T790M mutation. T790M is acquired resistance mutation in the exon 20 region. T790M is known to be generated by the use of existing EGFR inhibitors. The acquisition of T790M often decreases the effects of existing drug with respect to malignant tumor patients.

In the present invention, specifically, the EGFR having exon 18 and/or exon 21 mutation further having T790M mutation is preferably one of EGFR having E709X and/or G719X mutation in the exon 18 region further having T790M mutation, and EGFR having L861X mutation in the exon 21 region further having T790M mutation. In the present invention, more specifically, the EGFR having exon 18 and/or exon 21 mutation further having T790M mutation is preferably one of EGFR having E709K or E709A mutation further having T790M mutation, EGFR having G719A, G719S or G719C mutation further having T790M mutation, and EGFR having L861Q mutation further having T790M mutation. Among these, EGFR having G719A mutation further having T790M mutation and EGFR having L861Q mutation further having T790M mutation are particularly preferable.

In the present invention, the method for detecting exon 18 and/or exon 21 mutation of EGFR expressed by a malignant tumor patient is not particularly limited insofar as the method is capable of detecting the mutations, and any known detection methods may be used.

The sample used in the detection of exon 18 and/or exon 21 mutation is not particularly limited as long as the sample is a biological sample isolated from a malignant tumor patient, in particular, a sample obtained from a malignant tumor patient, and contains malignant tumor cells. Examples of biological samples include body fluids (e.g., blood, urine, etc.), tissues, the extracts thereof, and the cultures of obtained tissues. The method for obtaining a biological sample can be suitably selected depending on the type of biological sample.

The biological sample is prepared by being appropriately treated according to the measurement method. Further, the reagent comprising primer or probe used for the detection may be prepared by a conventional method according to the measurement method therefor.

In one embodiment of the present invention, a step of detecting the presence of exon 18 and/or exon 21 mutation of EGFR expressed by a malignant tumor patient may be performed before the administration of an antitumor agent to a malignant tumor patient.

A malignant tumor may include two or more different kinds of malignant tumor cells. Further, two or more malignant tumors may be generated in a single patient. Therefore, a single patient may have different mutations in the same amino acid position of EGFR (for example, the exon 18 mutation is G719A, G719S and G719C exon 18 mutation; E709K and E709A exon 18 mutation) at the same time.

The antitumor agent of the present invention comprises, as an active ingredient, (S)-N-(4-amino-6-methyl-5-(quinolin-3-yl)-8,9-dihydropyrimido[5,4-b]indolizin-8-yl)acrylamide (Compound (A)) or a salt thereof. Compound (A) is represented by the following chemical formula.

The method for producing the compound of the present invention is explained below.

Compound A of the present invention may be produced, for example, through the production method disclosed in WO2015/025936A1, the methods described in the Examples, and the like. However, the production method of the compound of the present invention is not limited to these reaction examples.

When Compound A of the present invention has isomers such as optical isomers, stereoisomers, and tautomers, any of the isomers and mixtures thereof are included within the scope of the compound of the present invention, unless otherwise specified. For example, when Compound A of the present invention has optical isomers, racemic mixtures and the optical isomers separated from a racemic mixture are also included within the scope of the compound of the present invention, unless otherwise specified.

The salts of Compound A refer to any pharmaceutically acceptable salts; examples include base addition salts and acid addition salts.

Examples of base addition salts include alkali metal salts such as sodium salts and potassium salts; alkaline earth metal salts such as calcium salts and magnesium salts; ammonium salts; and organic amine salts such as trimethylamine salts, triethylamine salts, dicyclohexylamine salts, ethanolamine salts, diethanolamine salts, triethanolamine salts, procaine salts, and N,N'-dibenzylethylenediamine salts.

Examples of acid addition salts include inorganic acid salts such as hydrochlorides, sulfates, nitrates, phosphates, and perchlorates; organic acid salts such as acetates, formates, maleates, fumarates, tartrates, citrates, ascorbates, and trifluoroacetates; and sulfonates such as methanesulfonates, isethionates, benzenesulfonates, and p-toluenesulfonates.

The compound of the present invention and salts thereof also encompass prodrugs thereof. A prodrug refers to a compound that can be converted to the compound of the present invention or a salt thereof through a reaction with an enzyme, gastric acid, or the like, under physiological conditions in vivo, i.e., a compound that can be converted to the compound of the present invention or a salt thereof by enzymatic oxidation, reduction, hydrolysis, or the like; or a compound that can be converted to the compound of the present invention or a salt thereof by hydrolysis or the like with gastric acid or the like. Further, the prodrug may be compounds that can be converted to the compound of the present invention or a salt thereof under physiological conditions, such as those described in "Iyakuhin no Kaihatsu [Development of Pharmaceuticals]," Vol. 7, Molecular Design, published in 1990 by Hirokawa Shoten Co., pp. 163-198.

Description of Diseases

Specific examples of tumors targeted in the present invention include, but are not particularly limited to, head and neck cancer, gastrointestinal cancer (esophageal cancer, stomach cancer, duodenal cancer, liver cancer, biliary cancer (e.g., gallbladder and bile duct cancer), pancreatic cancer, colorectal cancer (e.g., colon cancer, and rectal cancer), etc.), lung cancer (e.g., non-small-cell lung cancer, small-cell lung cancer, and mesothelioma), breast cancer, genital cancer (ovarian cancer, uterine cancer (e.g., cervical cancer, and endometrial cancer), etc.), urological cancer (e.g., kidney cancer, bladder cancer, prostate cancer, and testicular tumor), hematopoietic tumor (e.g., leukemia, malignant lymphoma, and multiple myeloma), osteosarcoma, soft-tissue sarcoma, skin cancer, brain tumor, and the like. Preferable examples include lung cancer, breast cancer, head and neck cancer, brain tumor, uterine cancer, digestive organ cancer, hematopoietic tumor, or skin cancer. Lung cancer is particularly preferable.

When Compound A or a salt thereof are used as a pharmaceutical agent, a pharmaceutical carrier can be added, if required, thereby forming a suitable dosage form according to prevention and treatment purposes. Examples of the dosage form include oral preparations, injections, suppositories, ointments, patches, and the like. Oral preparations are preferable. Such dosage forms can be formed by methods conventionally known to persons skilled in the art.

In one embodiment, the antitumor agent of the present invention is provided as a pharmaceutical composition comprising Compound A or a salt thereof, and a pharmaceutically acceptable carrier.

As the pharmaceutically acceptable carrier, various conventional organic or inorganic carrier materials used as preparation materials may be blended as an excipient, binder, disintegrant, lubricant, or colorant in solid preparations; or as a solvent, solubilizing agent, suspending agent, isotonizing agent, buffer, or soothing agent in liquid preparations. Moreover, pharmaceutical preparation additives, such as antiseptics, antioxidants, colorants, sweeteners, and stabilizers, may also be used, if required.

Oral solid preparations are prepared as follows. After an excipient is added optionally with an excipient, binder, disintegrant, lubricant, colorant, taste-masking or flavoring agent, etc., to the compound of the present invention, the resulting mixture is formulated into tablets, coated tablets, granules, powders, capsules, or the like by ordinary methods.

Examples of excipients include lactose, sucrose, D-mannitol, glucose, starch, calcium carbonate, kaolin, microcrystalline cellulose, and silicic acid anhydride. Examples of binders include water, ethanol, 1-propanol, 2-propanol, simple syrup, liquid glucose, liquid a-starch, liquid gelatin, D-mannitol, carboxymethyl cellulose, hydroxypropyl cellulose, hydroxypropyl starch, methyl cellulose, ethyl cellulose, shellac, calcium phosphate, polyvinylpyrrolidone, and the like. Examples of disintegrators include dry starch, sodium alginate, powdered agar, sodium hydrogen carbonate, calcium carbonate, sodium lauryl sulfate, stearic acid monoglyceride, lactose, and the like. Examples of lubricants include purified talc, sodium stearate, magnesium stearate, borax, polyethylene glycol, and the like. Examples of colorants include titanium oxide, iron oxide, and the like.

Examples of taste-masking or flavoring agents include sucrose, bitter orange peel, citric acid, tartaric acid, and the like.

When a liquid preparation for oral administration is prepared, a taste-masking agent, a buffer, a stabilizer, a flavoring agent, and the like may be added to the compound of the present invention; and the resulting mixture may be formulated into an oral liquid preparation, syrup, elixir, etc., according to an ordinary method.

When an injection agent is prepared, a pH regulator, a buffer, a stabilizer, an isotonizing agent, a local anesthetic, and the like, may be added to the compound of the present invention; and the mixture may be formulated into a subcutaneous, intramuscular, or intravenous injection according to an ordinary method.

Examples of the pH adjuster and the buffer used herein include sodium citrate, sodium acetate, and sodium phosphate. Examples of the stabilizer include sodium pyrosulfite, EDTA, thioglycolic acid, and thiolactic acid. Examples of the local anesthetic include procaine hydrochloride and lidocaine hydrochloride. Examples of the tonicity agent include sodium chloride, glucose, D-mannitol, and glycerol.

When a suppository is prepared, pharmaceutically acceptable carriers known in the related field, such as polyethylene glycol, lanolin, cacao butter, and fatty acid triglyceride; and as necessary, surfactants such as Tween 80 (registered trademark), may be added to Compound A, and the resulting mixture may be formulated into a suppository according to an ordinary method.

When an ointment is prepared, a commonly used base, stabilizer, wetting agent, preservative, and the like, may be blended into Compound A, as necessary; and the obtained mixture is mixed and formulated into an ointment according to an ordinary method.

Examples of the base include liquid paraffin, white petrolatum, white beeswax, octyl dodecyl alcohol, and paraffin. Examples of the preservative include methyl paraoxybenzoate, ethyl paraoxybenzoate, and propyl paraoxybenzoate.

When a patch is prepared, the above-described ointment, cream, gel, paste, or the like, may be applied to an ordinary substrate according to an ordinary method.

Examples of substrates include woven fabrics or non-woven fabrics comprising cotton, staple fibers, or chemical fibers; and films or foam sheets of soft vinyl chloride, polyethylene, polyurethane, etc., may also be used.

The amount of Compound A to be incorporated in each of such dosage unit forms depends on the condition of the patient to whom the compound is administered, the dosage form thereof, etc. In general, in the case of an oral agent, the amount of the compound is preferably 0.05 to 1000 mg per dosage unit form. In the case of an injection, the amount of the compound is preferably 0.01 to 500 mg per dosage unit form; and in the case of a suppository, the amount of the compound is preferably 1 to 1000 mg per dosage unit form.

Further, the daily dose of the medicine in such a dosage form depends on the condition, body weight, age, sex, etc., of the patient, and cannot be generalized or limited. Usually, the daily dose for an adult (body weight: 50 kg) of Compound A may generally be 0.05 to 5000 mg, and preferably 0.1 to 1000 mg; and is preferably administered in one dose, or in two to three divided doses, per day.

The present invention also provides a method for treating a malignant tumor patient, comprising the step of administering Compound A or a salt thereof to a malignant tumor patient expressing EGFR having exon 18 and/or exon 21 mutation.

The present invention also provides Compound A or a salt thereof for treating a malignant tumor patient expressing EGFR having exon 18 and/or exon 21 mutation.

The present invention also provides use of Compound A or a salt thereof for treating a malignant tumor patient expressing EGFR having exon 18 and/or exon 21 mutation.

The present invention also provides use of Compound A or a salt thereof for the production of a pharmaceutical agent for treating a malignant tumor patient expressing EGFR having exon 18 and/or exon 21 mutation.

The present invention also provides a pharmaceutical composition for treating a malignant tumor patient expressing EGFR having exon 18 and/or exon 21 mutation, the pharmaceutical composition comprising Compound A or a salt thereof, and a pharmaceutically acceptable carrier.

The present invention also provides a method for predicting therapeutic effects of chemotherapy using an antitumor agent comprising, as an active ingredient, Compound A or a salt thereof in a malignant tumor patient, the method comprising steps (1) and (2) below:

(1) a step of detecting the presence or absence of mutation of EGFR gene contained in a biological sample obtained from the patient; and (2) a step of predicting that the chemotherapy is highly likely to exhibit sufficient therapeutic effects to the patient when the results of the detection in step (1) found that the EGFR gene has exon 18 and/or exon 21 mutation.

The present invention also provides a method for treating a malignant tumor patient, comprising steps (1) to (3) below:

(1) a step of detecting the presence or absence of mutation of EGFR gene contained in a biological sample obtained from the patient; and (2) a step of predicting that chemotherapy using an antitumor agent comprising, as an active ingredient, (S)-N-(4-amino-6-methyl-5-(quinolin-3-yl)-8,9-dihydropyrimido[5,4-b]indolizin-8-yl)acrylamide or a salt thereof is highly likely to exhibit sufficient therapeutic effects with respect to the patient when the results of the detection in step (1) found that the EGFR gene has exon 18 and/or exon 21 mutation; and (3) a step of administering (S)-N-(4-amino-6-methyl-5-(quinolin-3-yl)-8,9-dihydropyrimido[5,4-b]indolizin-8-yl)acrylamide or a salt thereof to a malignant tumor patient who was predicted highly likely to sufficiently respond to the chemotherapy using an antitumor agent comprising, as an active ingredient, (S)-N-(4-amino-6-methyl-5-(quinolin-3-yl)-8,9-dihydropyrimido[5,4-b]indolizin-8-yl)actylamide or a salt thereof, in step (2).

The base sequence of EGFR gene is publicly known. The GenBank accession number of the base sequence of cDNA is NM_005228.4.

The "therapeutic effects" can be evaluated by tumor shrinkage effects, relapse-suppressing effects, life-prolonging effects, and the like. The relapse-suppressing effects may be shown as degree of the extension of non-relapse period or the degree of the improvement in relapse rate; and the life-prolonging effects may be shown as the degree of the entire survival time or the degree of the extension of the median of progression-free survival, or the like. The "sufficient therapeutic effects" of the chemotherapy using an antitumor agent comprising, as an active ingredient, Compound A or a salt thereof means, for example, that superior therapeutic effects are obtained by the administration of the antitumor agent comprising, as an active ingredient, Compound A or a salt thereof, such as extension of survival time, suppression of relapse, and the like, compared with non-administration.

EXAMPLES

The following describes the present invention in more detail with reference to the following Test Examples. However, the present invention is not limited to these Examples (Test Examples).

Test Example 1

In Vitro Drug Efficacy Test

Evaluation Results of Intracellular Phosphorylation in Mutant EGFR Forced Expression System Using HEK293 Cells (Inhibitory Activity)

The intracellular target inhibitory activity of compounds was evaluated based on the following as an index: intracellular EGFR phosphorylation in a mutant EGFR forced expression system using Jump-In (trademark) Grip (trademark) HEK293 cells (Thermo Fisher Scientific Inc.) (which may be hereinafter referred to as "HEK293 cells").

HEK293 cells were maintained in D-MEM with GlutalVIAX (trademark)-I (high-glucose) (Thermo Fisher Scientific Inc.) that contained 10% dialyzed FBS and 100 U/mL penicillin/100 µg/mL streptomycin (Thermo Fisher Scientific Inc.); and a pJTITM R4 DEST CMV pA vector to which a human EGFR gene (G719A, G719S, G719C, E709K, E709A, L861Q, G719A+T790M, or L861Q+T790M; the symbol "+" indicates that both mutations are contained) was encoded was introduced into HEK293 cells, together with Opti-MEM (trademark) I (Thermo Fisher Scientific Inc.), using a ViaFect (trademark) Transfection Reagent (Promega Corporation).

HEK293 cells expressing mutant human EGFR were seeded in each well of a 384-well flat-bottom microplate such that the cell count per well was 10,000, and incubated in a 5% CO2 gas-containing incubator at 37° C. for 1 day. Compound A, erlotinib, afatinib, and osimertinib (erlotinib, afatinib, and osimertinib may be each hereinafter referred to as a "comparative compound") were individually dissolved in DMSO, and diluted with DMSO or the medium used for suspending the cells. The solutions were then individually added to each well of the culture plate of the cells, and the cells were incubated in a 5% CO2 gas-containing incubator at 37° C. for 6 hours. After incubation, the cells were immobilized using 20% neutral buffered formalin (Wako Pure Chemical Industries, Ltd.), and blocked by an Odyssey (trademark) blocking buffer (PBS) (M&S TechnoSystems Inc.). The cells were then reacted with a primary antibody (EGFR Monoclonal Antibody (R19/48MIX) #AHR5062) (Thermo Fisher Scientific Inc.) that was diluted with an Odyssey (trademark) blocking buffer (PBS) to 1/200, and a Phospho-EGFR Receptor (Tyr1068) Antibody #2234L (CST)), followed by subjecting the cells to permeation at 4° C. overnight. The following day, the cells were reacted with a secondary antibody (IRDye 800CW Goat aRabbit #926-32211 and IRDye 680RD Goat aMouse #926-68070 (M&S TechnoSystems Inc.)) diluted with an Odyssey (trademark) blocking buffer (PBS) to 1/800, and subjected to permeation at room temperature for 1 hour. The fluorescence intensity (which may be hereinafter referred to as "FI") was detected with an Odyssey Infrared Imaging System (LI-COR Bioscience) at a fluorescence wavelength of 800 nm and 700 nm.

The value obtained by deducting the FI of a well without the cells from the FI detected at a fluorescence wavelength of 800 nm or 700 nm is referred to as FI (800, EGFR)-Blank (for 800 nm) and FI (700, p-EGFR)-Blank (for 700 nm). The value obtained by dividing FI (700, p-EGFR)-Blank of each well by FI (800, EGFR)-Blank was determined to be FI (p-EGFR/EGFR). The phosphorylated EGFR inhibitory rate was calculated using the following formula to determine the concentration of the test compounds at which phosphorylated EGFR was inhibited by 50% (IC50 (µM)). Table 1 illustrates the results.

Phosphorylated EGFR Inhibitory Rate (%)=T/C×100

T: FI (p-EGFR/EGFR) of a well to which a test compound was added.

C: FI (p-EGFR/EGFR) of a well to which a test compound was not added.

As is clear from Table 1, compound A exhibited high inhibitory activity against intracellular phosphorylation of exon 18 or exon 21 mutant EGFR, and the activity was higher than that of erlotinib or osimertinib, and was equivalent to that of afatinib. The inhibitory activity of compound A against exon 18 or exon 21 mutant EGFR was higher than that of afatinib in the presence of T790M mutation, which is an acquired resistant mutation.

TABLE 1

|  | Compound A of the Present Invention | Osimertinib | Afatinib | Erlotinib |
| --- | --- | --- | --- | --- |
| G719A | 20.5 | 237.0 | 20.0 | >1000 |
| G719S | 22.7 | 251.9 | 16.9 | 539.7 |
| G719C | 9.3 | 102.0 | 15.3 | 98.3 |
| E709K | 86.0 | 424.2 | 14.0 | 451.4 |
| E709A | 103.5 | 548.9 | 19.2 | 478.1 |
| L861Q | 40.5 | 143.1 | 24.7 | 608.1 |
| G719A + T790M | 31.3 | 132.1 | 110.2 | >1000 |
| L861Q + T790M | 81.8 | 132.4 | 177.6 | >1000 |

Test Example 2

Evaluation of Cell Growth Inhibitory Effect Against Wild-Type EGFR- and Mutant EGFR-Expressing Cell Line (In Vitro)

The inhibitory activity of compounds against wild-type EGFR and mutant EGFR was evaluated using Ba/F3 cells, which are mouse B-lymphocyte precursor cell line to which a human EGFR gene was introduced. Ba/F3 cells were maintained in an RPMI-1640 medium (Thermo Fisher Scientific Inc.) containing 10% fetal bovine serum (FBS), 100 U/mL penicillin/100 µg/mL streptomycin (Thermo Fisher Scientific Inc.), and 1 ng/mL mouse interleukin-3 (mIL-3) (CST). APB-CMV-MCS-EF1-GFP+Puro vector or PB-CMV-MCS-EF1-RFP+Puro vector into which a human EGFR gene (wild-type (WT), G719A, or L861Q) was encoded was introduced into the cells, together with a Super PiggyBac Transposase expression vector, by electroporation using an Amaxa (trademark) Cell Line Nucleofector (trademark) Kit V, followed by selection using puromycin (SIGMA). Ba/F3 cells expressing wild-type EGFR (which may be hereinafter referred to as "Ba/F3-EGFR_WT") exhibited mIL-3-independent growth in the presence of 50 ng/mL EGF (R&D Systems); and Ba/F3 cells expressing exon 18 or exon 21 active mutant EGFR (which may be hereinafter referred to as "Ba/F3-EGFR G719A," and "Ba/F3-EGFR L861Q") exhibited mIL-3-independent growth in the absence of EGF.

To evaluate a cell growth inhibitory effect, Ba/F3-EGFR_WT cells were suspended in an RPMI-1640 medium containing 10% FBS, 100 U/mL penicillin, 100 pg/mL streptomycin, and 50 ng/mL EGF; and the cell suspension was seeded in each well of a 96-well flat-bottom microplate such that the cell count per well was 30,000. Ba/F3-EGFR G719A cells and Ba/F3-EGFR L861Q cells were suspended in respective RPMI-1640 mediums containing 10% FBS, 100 U/mL penicillin, and 100 μg/mL streptomycin; and the cell suspensions were individually seeded in each well of a 96-well flat-bottom microplate such that the cell count per well was 15,000. Subsequently, compound A, gefitinib, erlotinib, afatinib, and osimertinib (gefitinib, erlotinib, afatinib, and osimertinib may be each hereinafter referred to as a "comparative compound") were individually dissolved in DMSO, and diluted with DMSO or the medium used for suspending the cells. The solutions were then added to each well of the culture plate of the cells, and the cells were incubated in a 5% $CO_2$ gas-containing incubator at 37° C. for 3 days. The cell count after incubation was measured by a CellTiter-Glo (trademark) Luminescent Cell Viability Assay (Promega Corporation) in accordance with the manufacturer's recommended protocol. The growth rate was calculated using the following formula to determine the concentration of each test compound for 50% inhibition (IC50 (μM)).

Growth Rate (%)=T/C×100

T: the luminescence intensity of a well to which a test compound was added.

C: the luminescence intensity of a well to which a test compound was not added.

The IC50 ratio between wild-type EGFR and G719A mutant EGFR, or between wild-type EGFR and L861Q mutant EGFR was determined using the following formula. Table 2 illustrates the results.

IC50 Ratio=IC50 (WT)/IC50 (G719A or L861Q)

As is clear from Table 2, compound A exhibited selective inhibitory activity against G719A mutation and L861Q mutation.

TABLE 2

|  | IC50 (nM) | | | IC50 Ratio | |
| --- | --- | --- | --- | --- | --- |
|  | WT | G719A | L861Q | WT/G719A | WT/L861Q |
| Compound A of the Present Invention | 597.3 | 9.0 | 19.0 | 66.4 | 31.4 |
| Osimertinib | 378.7 | 209.0 | 47.0 | 1.8 | 8.1 |
| Afatinib | 17.7 | 3.3 | 2.3 | 5.3 | 7.6 |
| Erlotinib | 778.3 | 336.3 | 353.0 | 2.3 | 2.2 |

Test Example 3

In Vivo Drug Efficacy Test

Evaluation of Antitumor Effect on Mouse Model Subcutaneously Transplanted with G719A Mutant EGFR-Expressing Cell Line The evaluation on mouse models subcutaneously transplanted with G719A mutant EGFR-expressing cell line was performed using NII-1-3T3 cells, which are mouse fibroblast cell line to which a human EGFR gene was introduced. NIH-3T3 cells were maintained in a D-MEM (high-glucose) medium (Wako Pure Chemical Industries, Ltd.) containing 10% newborn calf serum (NBCS), 1,500 mg/L sodium hydrogen carbonate, and 100 U/mL penicillin/100 μg/mL streptomycin (Thermo Fisher Scientific Inc.); and a PB-CMV-MCS-EF1-RFP+Puro vector into which a human EGFR gene (G719A) was encoded was introduced to the cells, together with a Super PiggyBac Transposase expression vector, by electroporation using an Amaxa (trademark) Cell Line Nucleofector (trademark) Kit R, followed by selection using puromycin (SIGMA). NIH-3T3 cells expressing exon 18 mutant EGFR (which may be hereinafter referred to as "NIH3T3-EGFR G719A") exhibited growth in the absence of EGF under 1% NBCS conditions.

In evaluation using mouse models subcutaneously transplanted with G719A mutant EGFR-expressing cell line, nude mice were subcutaneously transplanted with NIH3T3-EGFR G719A cells into which a mutant human EGFR was introduced. At the point at which the tumor volume of the tumor engrafted in the mice grew to about 100 to 200 mm3, the mice were allocated into groups, 5 or 6 mice for each group, by stratified randomization such that the average tumor volume between the groups was uniform. The mice were then orally administered compound A, afatinib, or osimertinib once daily for 14 consecutive days.

The dose of afatinib was 20 mg/kg/day, which is the maximum tolerated dose (the maximum dose at which the weight loss during a dosing period is less than 20%), for 14 days, the dosing period of this test. The dose of osimertinib was 25 mg/kg/day, which is a clinically efficacious dose. For compound A, three types of doses were set: 200 mg/kg/day (maximum tolerated dose), 100 mg/kg/day, and 50 mg/kg/day. The maximum tolerated dose was determined in accordance with the "Guidelines Involving Experimental Neoplasia Proposals in Mice and Rats" of the National Cancer Institute (NCI), from a humanitarian perspective.

To compare the changes in growth of tumor over time due to administration of the individual test compounds, the tumor volume (which may be hereinafter referred to as "TV") was used as an index. For a toxicity index, the body weight was measured over time, and the body weight change (which may be hereinafter referred to as "BWC (%)") from the day on which the mice were divided into groups was calculated in accordance with the following formula.

BWC (%)=(the body weight measured on body weight measurement day)/(the body weight on the day mice were divided into groups)

When the difference in the average TV between the control group and the group administered with a test compound on the final evaluation day was statistically significant (Dunnett's test, p<0.05), and the value of treatment/control (T/C) calculated using the following formula was less than 100, the test compound was determined to be effective. Such a case is indicated by the symbol "*" in the figures.

T/C (%)=(the average TV of the group administered with a test compound)/(the average TV of the control group)×100

Figure 1:
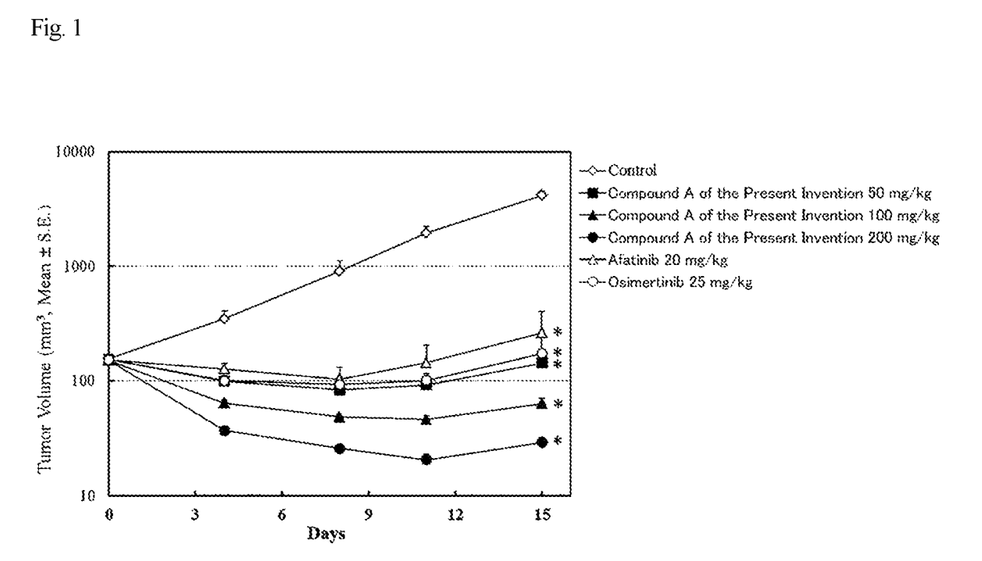
FIG. 1 illustrates the tumor volume (which may be hereinafter referred to as "TV") of mouse models subcutaneously transplanted with G719A mutant EGFR-expressing cell line to measure the antitumor effect of compound A.
Figure 2:
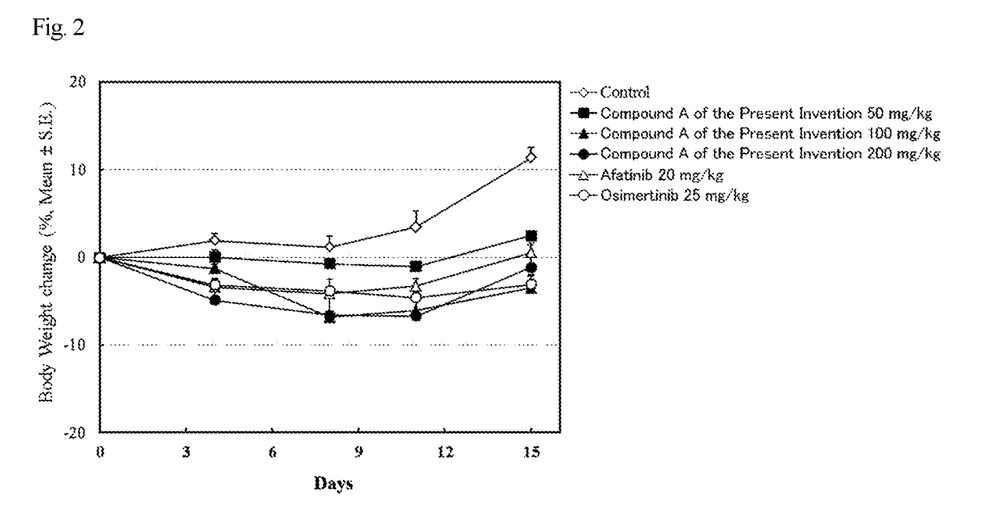
FIG. 2 illustrates the body weight change during a dosing period of compounds of mouse models subcutaneously transplanted with G719A mutant EGFR-expressing cell line to measure the toxicity of compound A.

As is clear from the results illustrated in FIG. 1, compound A of the present invention exhibited a remarkable antitumor effect on G719A mutant EGFR-expressing cell line subcutaneously transplanted into nude mice, accompanied by tumor regression. The effect was also higher than that of afatinib or osimertinib. The mice did not show symptoms, such as serious weight loss, as illustrated in FIG. 2, abnormal feces, or abnormal skin.

Test Example 4

In Vitro Drug Efficacy Test

Evaluation of Cell Growth Inhibitory Effect on T790M Mutant EGFR-Expressing Cell Line (In Vitro)

The inhibitory activity of a compound on T790M mutant EGFR was evaluated using Ba/F3 cells, which are mouse B-lymphocyte precursor cell line into which a human EGFR gene was introduced. Ba/F3 cells were maintained in an RPMI-1640 medium (Thermo Fisher Scientific Inc.) containing 10% fetal bovine serum (FBS), 100 U/mL penicillin/100 pg/mL streptomycin (Thermo Fisher Scientific Inc.), and 1 ng/mL mouse interleukin-3 (mIL-3) (CST); and a PB-CMV-MCS-EF1-GFP+Puro vector or PB-CMV-MCS-EF1-RFP+Puro vector into which a human EGFR gene (wild-type (WT), G719A+T790M, or L861Q+T790M) was encoded was introduced into the cells, together with a Super PiggyBac Transposase expression vector, by electroporation using an Amaxa (trademark) Cell Line Nucleofector (trademark) Kit V, followed by selection using puromycin (SIGMA). Ba/F3 cells expressing G719A+T790M mutant EGFR or L861Q+T790M mutant EGFR (which may be hereinafter referred to as "Ba/F3-EGFR G719A+T790M," and "Ba/F3-EGFR L861Q+T790M") exhibited mIL-3-independent growth in the absence of EGF.

To evaluate a cell growth inhibitory effect, Ba/F3-EGFR G719A+T790M cells and Ba/F3-EGFRL861Q+T790M cells were individually suspended in an RPMI-1640 medium containing 10%1-13S, 100 U/mL penicillin, and 100 μg/mL streptomycin; and the cell suspensions were individually seeded in each well of a 96-well flat-bottom microplate such that the cell count per well was 15,000. Subsequently, compound A, gefitinib, erlotinib, afatinib, and osimertinib (gefitinib, erlotinib, afatinib, and osimertinib may be each hereinafter referred to as a "comparative compound") were individually dissolved in DMSO, and diluted with DMSO or the medium used for suspending the cells. These solutions were then added to each well of the culture plate of the cells, and incubated in a 5% CO2 gas-containing incubator at 37° C. for 3 days. The cell count after incubation was measured using a CellTiter-Glo (trademark) Luminescent Cell Viability Assay (Promega Corporation), in accordance with the manufacturer's recommended protocol. The growth rate was calculated using the following formula to determine the concentration of each test compound for 50% inhibition (IC50 (μM)).

Growth Rate (%)=T/C×100

T: the luminescence intensity of a well to which a test compound was added.
C: the luminescence intensity of a well to which the test compound was not added.

Additionally, the IC50 ratio between wild-type EGFR and G719A+T790M mutant EGFR, or between wild-type EGFR and L861Q+T790M mutant EGFR was calculated using the following formula. Table 3 illustrates the results.

IC50 Ratio=IC50 (WT)/IC50 (G719A+T790M or L861Q+T790M)

As is clear from Table 3, compound A exhibited selective inhibitory activity against G719A+T790M mutation and L861Q+T790M mutation.

TABLE 3

|  | IC50 (nM) | | IC50 Ratio | |
| --- | --- | --- | --- | --- |
|  | G719A + T790M | L861Q + T790M | WT/G719A + T790M | WT/L861Q + T790M |
| Compound A of the Present Invention | 15.8 | 37.5 | 37.9 | 15.9 |
| Osimertinib | 89.4 | 36.4 | 4.2 | 10.4 |
| Afatinib | 68.2 | 168.7 | 0.3 | 0.1 |
| Erlotinib | 8030.0 | 6424.2 | 0.1 | 0.1 |

Test Example 5

In Vivo Drug Efficacy Test

Evaluation of Antitumor Effect on Mouse Model Subcutaneously Transplanted with G719A+T790M Mutant EGFR-Expressing Cell Line The evaluation of mouse models subcutaneously transplanted with G719A+T790M mutant EGFR-expressing cell line was performed using NII-1-3T3 cells, which are mouse fibroblast cell line into which a human EGFR gene was introduced. NII-1-3T3 cells were maintained in a D-MEM (high-glucose) medium (Wako Pure Chemical Industries, Ltd.) containing 10% newborn calf serum (NBCS), 1,500 mg/L sodium hydrogen carbonate, and 100 U/mL penicillin/100 pg/mL streptomycin (Thermo Fisher Scientific Inc.); and a PB-CMV-MCS-EF1-RFP+Puro vector into which a human EGFR gene (G719A+T790M) was encoded was introduced to the cells, together with a Super PiggyBac Transposase expression vector, by electroporation using an Amaxa (trademark) Cell Line Nucleofector (trademark) Kit R, followed by selection using puromycin (SIGMA). NII-1-3T3 cells expressing exon 18 mutant EGFR (which may be hereinafter referred to as "NIH3T3-EGFR G719A+T790M") exhibited growth in the absence of EGF under 1% NBCS conditions.

In evaluation using mouse models subcutaneously transplanted with G719A+T790M mutant EGFR-expressing cell line, nude mice were subcutaneously transplanted with NIH3T3-EGFR G719A+T790M cells into which mutant human EGFR was introduced. At the point at which the tumor volume of the tumor engrafted in the mice grew to about 100 to 300 mm3, the mice were allocated into groups, 5 mice for each group, by stratified randomization such that the average tumor volume between the groups was uniform. The mice were then orally administered compound A of the present invention or afatinib once daily on consecutive days.

The dose of afatinib was 20 mg/kg/day, which is the maximum tolerated dose (the maximum dose at which the weight loss during a dosing period is less than 20%), for 14 days, the dosing period of this test. For compound A of the present invention, three types of doses were set: 200 mg/kg/day (maximum tolerated dose), 100 mg/kg/day, and 50 mg/kg/day. The maximum tolerated dose was determined in accordance with the "Guidelines Involving Experimental Neoplasia Proposals in Mice and Rats" of the National Cancer Institute (NCI), from a humanitarian perspective.

Figure 3:
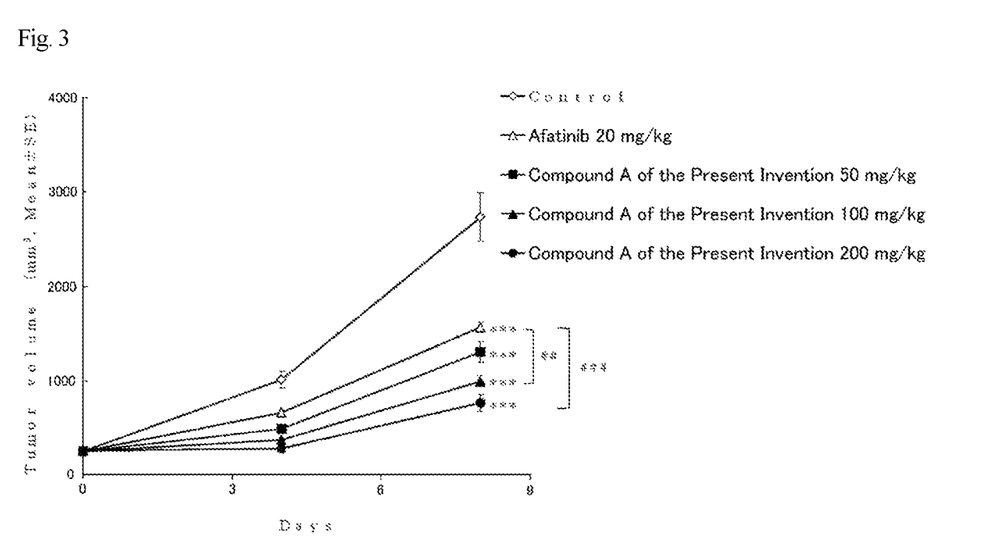
FIG. 3 illustrates the tumor volume of mouse models subcutaneously transplanted with G719A+T790M mutant EGFR-expressing cell line to measure the antitumor effect of compound A.
Figure 4:
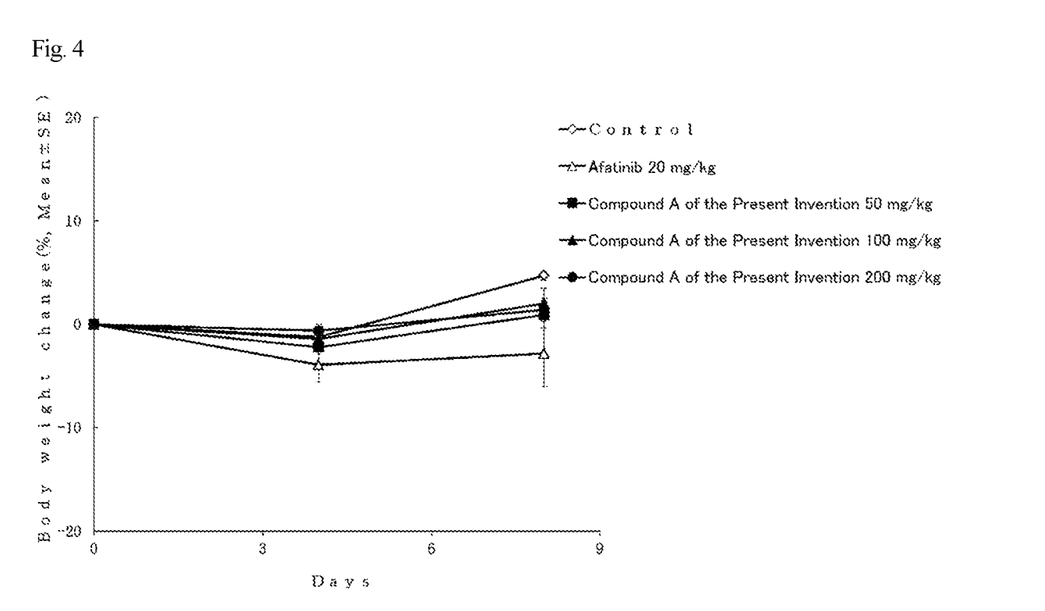
FIG. 4 illustrates the body weight change during a dosing period of compounds of mouse models subcutaneously transplanted with G719A+T790M mutant EGFR-expressing cell line to measure the toxicity of compound A.

To compare the changes in growth of tumor over time due to administration of the individual test compounds, the tumor volume (which may be hereinafter referred to as "TV") was used as an index. FIG. 3 illustrates changes in TV over time. For a toxicity index, the body weight was measured over time, and the body weight change (which may be hereinafter referred to as "BWC (%)") from the day on which the mice were divided into groups was calculated in accordance with the following formula. FIG. 4 illustrates changes in body weight over time.

BWC (%)=(the body weight measured on body weight measurement day)/(the body weight on the day mice were divided into groups)

A Dunnett's test was performed using the average TV on the final evaluation day as an index. When the difference in the average TV between the control group and the group administered with a test compound was statistically significant ($p < 0.05$), and the value of treatment/control (T/C) calculated using the following formula was less than 100, the test compound was determined to be effective. Such a case is indicated by the symbol "*" in FIG. 3 and Table 4 (*: p<0.05, : p<0.01, *: p<0.001). Additionally, when the difference in the average TV between the group administered with compound A of the present invention and the group administered with afatinib was statistically significant (p<0.05), and the T/C value of the group administered with compound A of the present invention was smaller than the T/C value of the group administered with afatinib, compound A was determined to have a higher antitumor effect than afatinib. Such a case is indicated by the symbol "#" in FIG. 3 and Table 4 (#: p<0.05,/* p<0.01, p<0.001).

T/C (%)=(the average TV of the group administered with a test compound)/(the average TV of the control group)×100

As is clear from the results illustrated in FIG. 3, compound A of the present invention exhibited a significant antitumor effect on G719A+T790M mutant EGFR-expressing cell line subcutaneously transplanted into nude mice. Additionally, as shown in Table 4, the effect was higher than that of afatinib, without symptoms such as serious weight loss (as illustrated in FIG. 4), abnormal feces, or abnormal skin in mice.

TABLE 4

| Compound | Dose (mg/kg) | T/C (%) | p value vs Control | p value vs Afatinib |
|---|---|---|---|---|
| Control | — | 100.0 | — | — |
| Compound A of the Present Invention | 50 | 47.7 | *** | N.S. |
| Compound A of the Present Invention | 100 | 36.4 | *** | ## |
| Compound A of the Present Invention | 200 | 28.0 | *** | ### |
| Afatinib | 20 | 57.4 | *** | — |

N.S.: No Significant Difference
***: p < 0.001 (Dunnett's test vs Control Group)
: p < 0.01 (Dunnett's test vs Afatinib Group)
: p < 0.001 (Dunnett's test vs Afatinib Group)

---

The invention claimed is:

1. A method for treating a subject with a malignant tumor, comprising:
    administering (S)-N-(4-amino-6-methyl-5-(quinolin-3-yl)-8,9-dihydropyrimido[5,4-b]indolizin-8-yl)acrylamide or a salt thereof to a subject with a malignant tumor expressing EGFR having at least one mutation selected from the group consisting of G719X mutation of exon 18, E709X mutation of exon 18, and L1861X mutation of exon 21, wherein G719X indicates glycine at position 719 is replaced by another amino acid, E709X indicates glutamate at position 709 is replaced by another amino acid, and L861X indicates leucine at position 861 is replaced by another amino acid.

2. The method according to claim 1, wherein the exon 18 mutation is at least one mutation selected from the group consisting of G719A, G719S, G719C, E709K and E709A.

3. The method according to claim 1, wherein the exon 21 mutation is L861Q.

4. The method according to claim 1, wherein the EGFR further has T790M mutation.

5. A method for treating a subject with a malignant tumor patient, comprising:
    the step of administering a pharmaceutical composition comprising (S)-N-(4-amino-6-methyl-5-(quinolin-3-yl)-8,9-dihydropyrimido[5,4-b]indolizin-8-yl)acrylamide or a salt thereof and a pharmaceutically acceptable carrier, to a subject with a malignant tumor expressing EGFR having at least one mutation selected from the group consisting of G719X mutation of exon 18, E709X mutation of exon 18, and L861X mutation of exon 21, wherein G719X indicates glycine at position 719 is replaced by another amino acid, E709X indicates glutamate at position 709 is replaced by another amino acid, and L861X indicates leucine at position 861 is replaced by another amino acid.

6. The method according to claim 5, wherein the exon 18 mutation is at least one mutation selected from the group consisting of G719A, G719S, G719C, E709K and E709A.

7. The method according to claim 5, wherein the exon 21 mutation is L861Q.

8. The method according to claim 5, wherein the EGFR further has T790M mutation.

9. A method for predicting therapeutic effects of chemotherapy using an antitumor agent comprising, as an active ingredient, (S)-N-(4-amino-6-methyl-5-(quinolin-3-yl)-8,9-dihydropyrimido[5,4-b]indolizin-8-yl)acrylamide or a salt thereof in a subject with a malignant tumor, the method comprising:
    detecting the presence or absence of mutation of EGFR gene contained in a biological sample obtained from the the subject; and
    predicting that the chemotherapy is highly likely to exhibit sufficient therapeutic effects with respect to the subject when the results of the detecting found that the EGFR gene has at least one mutation selected from the group consisting of G719X mutation of exon 18, E709X mutation of exon 18, and L861X mutation of exon 21, wherein G719X indicates glycine at position 719 is replaced by another amino acid, E709X indicates glutamate at position 709 is replaced by another amino acid, and L861X indicates leucine at position 861 is replaced by another amino acid.

10. The method according to claim 9, wherein the exon 18 mutation is at least one mutation selected from the group consisting of G719A, G719S, G719C, E709K and E709A.

11. The method according to claim 9, wherein the exon 21 mutation is L861Q.

12. The method according to claim 9, wherein the EGFR further has T790M mutation.

13. A method for treating a subject with a malignant tumor, comprising:

detecting the presence or absence of mutation of EGFR gene contained in a biological sample obtained from the subject;

predicting that chemotherapy using an antitumor agent comprising, as an active ingredient, (S)-N-(4-amino-6-methyl-5-(quinolin-3-yl)-8,9-dihydropyrimido[5,4-b]indolizin-8-yl)acrylamide or a salt thereof is highly likely to exhibit sufficient therapeutic effects with respect to the atient subject when the results of the detecting found that the EGFR gene has at least one mutation selected from the group consisting of G719X mutation of exon 18, E709X mutation of exon 18, and L861X mutation of exon 21, G719X indicates glycine at position 719 is replaced by another amino acid, E709X indicates glutamate at position 709 is replaced by another amino acid, and L861X indicates leucine at position 861 is replaced by another amino acid; and administering (S)-N-(4-amino-6-methyl-5-(quinolin-3-yl)-8,9-dihydropyrimido[5,4-b]indolizin-8-yl)acrylamide or a salt thereof to a subject with a malignant tumor who was predicted highly likely to sufficiently respond to the chemotherapy using an antitumor agent comprising, as an active ingredient, (S)-N-(4-amino-6-methyl-5-(quinolin-3-yl)-8,9-dihydropyrimido[5,4-b]indolizin-8-yl)acrylamide or a salt thereof.

14. The method according to claim 13, wherein the exon 18 mutation is at least one mutation selected from the group consisting of G719A, G719S, G719C, E709K and E709A.

15. The method according to claim 13, wherein the exon 21 mutation is L861Q.

16. The method according to claim 13, wherein the EGFR further has T790M mutation.

17. The method according to claim 1, wherein the malignant tumor is lung cancer.

18. The method according to claim 1, wherein the malignant tumor is lung cancer, head and neck cancer, or brain tumor.

19. The method according to claim 1, wherein the malignant tumor is breast cancer, colorectal cancer, or pancreatic cancer.

20. The method according to claim 5, wherein the malignant tumor is lung cancer.

21. The method according to claim 5, wherein the malignant tumor is lung cancer, head and neck cancer, or brain tumor.

22. The method according to claim 5, wherein the malignant tumor is breast cancer, colorectal cancer, or pancreatic cancer.

23. The method according to claim 9, wherein the malignant tumor is lung cancer.

24. The method according to claim 9, wherein the malignant tumor is lung cancer, head and neck cancer, or brain tumor.

25. The method according to claim 9, wherein the malignant tumor is breast cancer, colorectal cancer, or pancreatic cancer.

26. The method according to claim 13, wherein the malignant tumor is lung cancer.

27. The method according to claim 13, wherein the malignant tumor is lung cancer, head and neck cancer, or brain tumor.

28. The method according to claim 13, wherein the malignant tumor is breast cancer, colorectal cancer, or pancreatic cancer.

* * * * *

UNITED STATES PATENT AND TRADEMARK OFFICE
CERTIFICATE OF CORRECTION

| | | |
|---|---|---|
| PATENT NO. | : 11,701,359 B2 | Page 1 of 1 |
| APPLICATION NO. | : 16/642969 | |
| DATED | : July 18, 2023 | |
| INVENTOR(S) | : Abe et al. | |

It is certified that error appears in the above-identified patent and that said Letters Patent is hereby corrected as shown below:

On the Title Page

Column 2, item (56), under "Other Publication", Line 6, delete "charactertistics" and insert -- characteristics --, therefor.

Column 2, item (56), under "Other Publication", Line 22, delete ""Structual," and insert -- "Structural, --, therefor.

On Page 2, Column 1, item (56), under "Other Publication", Line 27, delete "non-mall" and insert -- non-small --, therefor.

On Page 2, Column 2, item (56), under "Other Publication", Line 47, delete "Mutationsand" and insert -- Mutations and --, therefor.

In the Claims

In Column 25, Claim 1, Line 40, delete "L1861X" and insert -- L861X --, therefor.

In Column 25, Claim 5, Line 54, before "comprising", delete "patient,".

In Column 25, Claim 5, Line 55, before "administering", delete "the steps of".

In Column 26, Claim 9, Line 47, delete "the the" and insert -- the --, therefor.

In Column 27, Claim 13, Line 10, before "subject", delete "atient".

In Column 27, Claim 13, Line 13, after "exon 21," insert -- wherein --.

Signed and Sealed this
Eighth Day of October, 2024

*Katherine Kelly Vidal*

Katherine Kelly Vidal
*Director of the United States Patent and Trademark Office*